(12) United States Patent
Horita et al.

(10) Patent No.: US 9,962,498 B2
(45) Date of Patent: May 8, 2018

(54) SYRINGE

(71) Applicant: Taisei Kako Co., Ltd., Osaka-shi, Osaka (JP)

(72) Inventors: Taiji Horita, Osaka (JP); Ippei Matsumoto, Osaka (JP); Kensuke Taniguchi, Osaka (JP)

(73) Assignee: Taisei Kako Co., Ltd., Osaka (JP)

( * ) Notice: Subject to any disclaimer, the term of this patent is extended or adjusted under 35 U.S.C. 154(b) by 0 days. days.

(21) Appl. No.: 14/435,992

(22) PCT Filed: Oct. 24, 2013

(86) PCT No.: PCT/JP2013/078755
§ 371 (c)(1),
(2) Date: Apr. 15, 2015

(87) PCT Pub. No.: WO2014/065345
PCT Pub. Date: May 1, 2014

(65) Prior Publication Data
US 2015/0335830 A1    Nov. 26, 2015

(30) Foreign Application Priority Data
Oct. 25, 2012  (JP) ................. 2012-235668

(51) Int. Cl.
*A61M 5/32*   (2006.01)
*A61M 5/20*   (2006.01)
*A61M 5/31*   (2006.01)

(52) U.S. Cl.
CPC ........ *A61M 5/3213* (2013.01); *A61M 5/3204* (2013.01); *A61M 5/20* (2013.01);
(Continued)

(58) Field of Classification Search
CPC ..... A61M 5/3204; A61M 5/32; A61M 5/3213
See application file for complete search history.

(56) References Cited

U.S. PATENT DOCUMENTS 5,980,495 A    11/1999 Heinz et al.
6,287,279 B1 *  9/2001 Siekmann ............. A61M 5/322
                                              604/110
(Continued)

FOREIGN PATENT DOCUMENTS

EP    1208861 A1    5/2002
EP    1795220 A     6/2007
(Continued)

OTHER PUBLICATIONS

International Preliminary Report on Patentability issued May 7, 2015 in connection with PCT/JP2013/078755.
(Continued)

*Primary Examiner* — Nathan R Price
*Assistant Examiner* — Melissa A Snyder
(74) *Attorney, Agent, or Firm* — Berliner & Associates

(57) ABSTRACT

An object is to provide a syringe that is capable of preventing a cap from being mounted to a syringe body at an oblique angle. The cap includes an elastic cylindrical body for receiving an injection needle therein and sealing a holding part, and an external cylindrical body for covering the circumference of the elastic cylindrical body and holding the elastic cylindrical body in such a manner as to prevent movement of the elastic cylindrical body. The external cylindrical body includes an opening part having a dimension configured to be larger than the holding part of the syringe body, and a guide part that guides the injection needle toward a certain direction by coming into contact with a part of the syringe body when the injection needle is received inside the elastic cylindrical body.

10 Claims, 11 Drawing Sheets

(52) U.S. Cl.
 CPC .............. *A61M 2005/3109* (2013.01); *A61M 2005/3215* (2013.01); *A61M 2205/02* (2013.01); *A61M 2205/0216* (2013.01)

(56) References Cited

U.S. PATENT DOCUMENTS

| | | | | |
|---|---|---|---|---|
| 6,719,732 | B2 * | 4/2004 | Courteix | A61M 5/3202 604/192 |
| 7,641,636 | B2 * | 1/2010 | Moesli | A61M 5/3202 604/162 |
| 2008/0255521 | A1 * | 10/2008 | Kubo | A61M 5/284 604/191 |

FOREIGN PATENT DOCUMENTS

| | | | | |
|---|---|---|---|---|
| JP | H05-032069 | A | 5/1993 | |
| JP | H10-305098 | A | 11/1998 | |
| JP | 2003-24415 | A | 1/2003 | |
| JP | 2003-24439 | A | 1/2003 | |
| WO | WO 2011098831 | A1 * | 8/2011 | .......... A61M 5/3213 |
| WO | WO2011114917 | A1 | 9/2011 | |

OTHER PUBLICATIONS

European Search Report issued Jul. 15, 2016 in connection with related European Patent Appl. No. 13849547.8.

\* cited by examiner

SYRINGE

CROSS-REFERENCE TO RELATED APPLICATION

This application claims priority to Japanese Patent Application No. 2012-235668, the disclosure of which is incorporated herein by reference in its entirety.

FIELD

The present invention relates to a syringe provided with a cap covering an injection needle.

BACKGROUND

Pre-filled syringes each being filled with a certain injection solution of a certain volume are used in many medical fields since they enable accurate administration of a certain injection solution in a certain volume without error. As the pre-filled syringes of this type, a so-called injection needle mounting pre-filled syringe, in which an injection needle is previously secured to a distal end of a syringe body (barrel) has been used in many medical fields.

For the injection needle mounting pre-filled syringe, a cap for protecting the injection needle is used. This cap (needle shield assembly) has a two layer structure including an outer layer portion (shield) made of a transparent resin, and an inner layer portion (sheath) having elasticity (see Patent Literature 1, for example). This cap has an inner layer portion entire formed on the entire inner surface of an outer layer portion.

CITATION LIST

Patent Literature

Patent Literature 1: JP-1993-032069 B

SUMMARY

Technical Problem

There may cause a case in the conventional cap, in which the injection needle is positioned at an oblique angle relative to the axial direction of the cap when the injection needle is inserted into the cap. As a result, the cap is mounted to the syringe body at an oblique angle thereto.

Mounting of the cap at an oblique angle to the syringe body makes it difficult for the syringe to be housed in a nest for storage and transportation, for example, during the manufacturing process of syringes. Furthermore, there may cause a possibility of damaging a syringe. When a syringe is used for an apparatus which is called an auto injector that is capable of automatically injecting a medicinal solution at a constant speed, there may cause a problem in which the cap is not appropriately mounted to the auto injector.

Furthermore, there may cause an event in which the injection needle obliquely is inserted to stab into the inner layer portion, ruptures the inner layer, and hence the sealing performance cannot be maintained.

In consideration of the above circumstances, an object of the present invention is to provide a syringe that is capable of preventing the cap from being mounted to the syringe body at an oblique angle.

Solution to Problem

According to the present invention, there is provided a syringe including a syringe body that includes a holding part for holding an injection needle, and a cap for covering the injection needle. The cap includes an elastic cylindrical body for receiving the injection needle therein and sealing the holding part, and an external cylindrical body for covering the circumference of the elastic cylindrical body and holding the elastic cylindrical body in such a manner as to prevent movement of the elastic cylindrical body. The external cylindrical body includes an opening part having a dimension configured to be larger than the holding part of the syringe body, and a guide part that guides the injection needle toward a certain direction by coming into contact with a part of the syringe body when the injection needle is received inside the elastic cylindrical body.

According to the syringe of the present invention, the guide part may include a ridge for contacting a part of the syringe body.

According to the syringe of the present invention, the syringe body may include a ridge for contacting the guide part.

According to the syringe of the present invention, the guide part may have a cylindrical shape, and an outer surface of a part of the syringe body may have a circular shape so as to contact an inner surface of the guide part.

According to the syringe of the present invention, it may be configured such that: the external cylindrical body has one end provided with the opening part therein, and another end provided with a closing part; the external cylindrical body includes a protrusion that protrudes inwardly from the closing part in the tube axis direction of the external cylindrical body, and a locking ridge that comes into locking engagement with the elastic cylindrical body to lock the elastic cylindrical body at a certain position of an inner surface of the external cylindrical body, the certain position being distant from the protrusion; the external cylindrical body holds the elastic cylindrical body with the protrusion and the locking ridge sandwiching the elastic cylindrical body; and a distance between the protrusion and the locking ridge is smaller than a length of the elastic cylindrical body.

According to the syringe of the present invention, the syringe body may be made of cycloolefin polymer.

DESCRIPTION OF EMBODIMENTS

Figure 1:
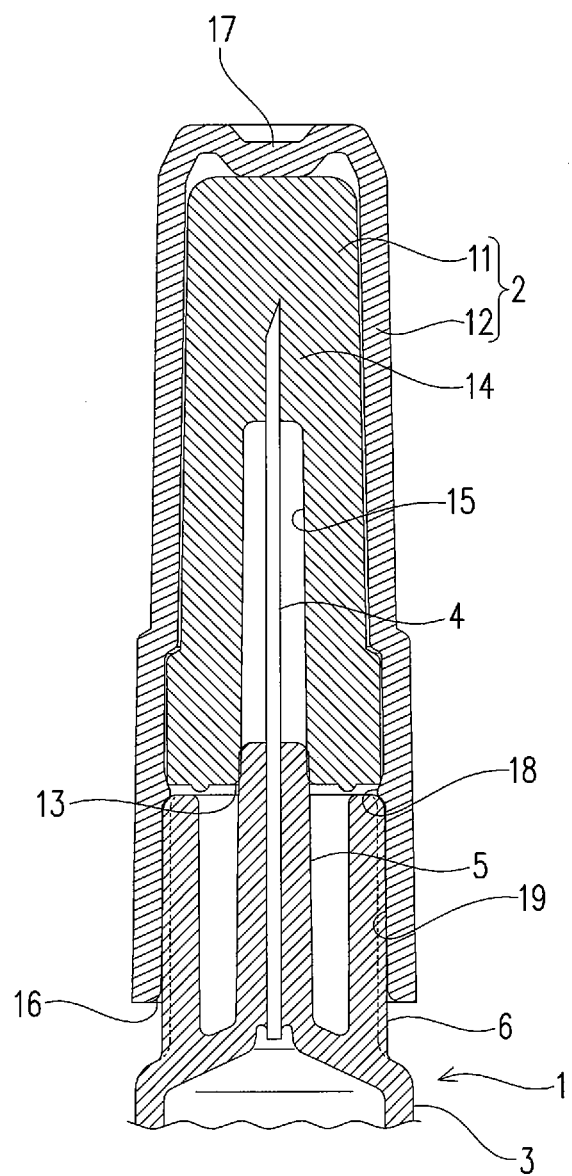
FIG. 1 is a cross sectional view showing a first embodiment of a syringe according to the present invention.

The description is hereinafter made for an embodiment carrying out the present invention with reference to the attached drawings. FIG. 1 shows a first embodiment of a syringe according to the present invention.

As shown in FIG. 1, the syringe includes a syringe body 1, and a cap mounted to the syringe body 1. The syringe body 1 has a tubular shape made of glass or a transparent synthetic resin. The syringe body 1 is preferably made of polyolefin (including cyclic polyolefin, such as cycloolefin copolymer (COC) and cycloolefin polymer), especially preferably made of cycloolefin polymer. Cycloolefin polymer has high dimensional stability and small shrinkage ratio so that the syringe body 1 made of this material can be molded with good accuracy.

The syringe body 1 includes a tubular shank 3, an injection needle 4, a holding part 5 for holding the injection needle 4, and a tubular part 6 formed around the holding part 5.

The shank 3 is configured as a cylindrical body having a certain length. The shank 3 has one end which is sealed, and the holding part 5 is integrally formed with this sealed end. Although not shown, an opening part is formed at another end of the shank 3 so that a plunger (not shown) can be inserted through this opening part.

The holding part 5 is a ridge part that projects from the one end of the shank 3. The holding part 5 projects along the center axis of the shank 3. The holding part 5 has a cylindrical shape. The injection needle 4 is placed inside the holding part 5.

The tubular part 6 has a cylindrical shape. The tubular part 6 has an inner diameter larger than the outer diameter of the holding part 5. The tubular part 6 is arranged coaxially with the holding part 5 to cover the holding part 5. The tubular part 6 has a length smaller than the length of the holding part 5. Accordingly, the holding part 5 has its distal end further projecting outward than the distal end of the tubular part 6.

As shown in FIG. 1, a cap 2 includes an elastic cylindrical body 11 for receiving the injection needle 4 therein and sealing the holding part 5, and an external cylindrical body 12 for covering the circumference of the elastic cylindrical body 11 and holding the elastic cylindrical body 11 in such a manner as to prevent movement of the elastic cylindrical body 11.

The elastic cylindrical body 11 is made of an elastic material such as rubber and has a cylindrical shape. The elastic cylindrical body 11 has one end provided with an opening part 13 therein, and another end provided with a closing part 14. With this configuration, the elastic cylindrical body 11 has an insertion recess 15 into which the injection needle 4 is inserted. The elastic cylindrical body 11 is configured to have a small outer diameter on the closing part 14 side, and a large outer diameter on the opening part 13 side.

The external cylindrical body 12 is made of a material harder than the material of the elastic cylindrical body 11. The external cylindrical body 12 is made of, for example, a transparent synthetic resin and has a cylindrical shape. The external cylindrical body 12 has an inner circumferential surface having a circular shape in cross section. The syringe body 1 has a circular outer circumferential surface. The external cylindrical body 12 has an entire length greater than the entire length of the elastic cylindrical body 11.

The external cylindrical body 12 has one end provided with an opening part 16 therein, and another end provided with a closing part 17. The diameter of the opening part 16 of the external cylindrical body 12 is configured to be larger than the outer diameter of the holding part 5 of the syringe body 1. The diameter of the opening part 16 of the external cylindrical body 12 is substantially equal to the outer diameter of the tubular part 6 that is a part of the syringe body 1. The external cylindrical body 12 is configured to have a small diameter on the closing part 17 side, and a large diameter on the opening part 16 side. The external cylindrical body 12 includes a locking ridge 18 that comes into locking engagement with the elastic cylindrical body 11, and a guide part 19 that guides the injection needle 4 toward a certain direction by coming into contact with a part of the syringe body 1 when the injection needle 4 is received inside the elastic cylindrical body 11.

The locking ridge 18 is formed on an inner surface at an intermediate part of the external cylindrical body 12. The locking ridge 18 projects from the inner surface of the external cylindrical body 12 toward the radially inner side of the external cylindrical body 12. The locking ridge 18 has an annular shape extending along the inner circumferential direction of the external cylindrical body 12. The external cylindrical body 12 is configured to sandwich the elastic cylindrical body 11 between an inner surface of the closing part 17 and the locking ridge 18.

The elastic cylindrical body 11 is held by the closing part 17 and the locking ridge 18 of the external cylindrical body 12 so as to be prevented from slipping out. In order to secure this holding, a strength (connection strength) of such a magnitude as to prevent the elastic cylindrical body 11 from slipping out from the external cylindrical body 12 when the elastic cylindrical body 11 has been pulled with a force of, for example, 60 N is required.

The guide part 19 is formed on a portion between the opening part 16 of the external cylindrical body 12 and the locking ridge 18. Since the entire length of the external cylindrical body 12 is greater than the entire length of the elastic cylindrical body 11, the external cylindrical body 12 has a part non-overlapping with the elastic cylindrical body 11, when the elastic cylindrical body 11 is inserted into the deepest part of the external cylindrical body 12. In the present embodiment, this part acts as the guide part 19.

The guide part 19 has a cylindrical shape. The guide part 19 is configured to be coaxial with the external cylindrical body 12, and is configured to be coaxial with the elastic cylindrical body 11 held inside the external cylindrical body 12. The guide part 19 has an inner surface that comes into contact with the outer surface of the tubular part 6. The length of the guide part 19 in the tube axis direction is configured to be greater than the length of the holding part 5 of the syringe body 1. The inner diameter of the guide part 19 is configured to be substantially equal to the outer diameter of the tubular part 6 of the syringe body 1.

The description is hereinafter given for the action produced by the mounting of the cap 2 to the syringe body 1. When the cap 2 is mounted to the syringe body 1, the injection needle 4 of the syringe body 1 is first inserted through the opening part 16 of the elastic cylindrical body 11. Then, the injection needle 4 is inserted into the inside the elastic cylindrical body 11 through the opening part 13 of the elastic cylindrical body 11. Then, the holding part 5 of the syringe body 1 is inserted into the inside portion through the opening part 16 of the external cylindrical body 12. Just after that, the tubular part 6 of the syringe body 1 is inserted into the inside the external cylindrical body 12 of the cap 2 through the opening part 12. At this time, the outer surface of the tubular part 6 of the syringe body 1 comes into contact with the inner surface of the guide part 19.

In this state, when the cap 2 is pressed, the tubular part 6 of the syringe body 1 moves linearly toward the deepest part of the cap 2 while being guided by the guide part 19. Whereby, the contact surface of the tubular part 6 of the syringe body 1 which is in contact with the guide part 19 is increased. Then, the injection needle 4 is pierced into the bottom surface of the insertion recess 15 of the elastic cylindrical body 11. At this time, since the guide part 19 guides the syringe body 1, the injection needle 4 is pierced into the bottom surface of the insertion recess 15 along the axial direction of the cap 2 without being tilted.

Then, the distal end of the holding part 5 is inserted into the opening part 13 of the elastic cylindrical body 11. At this time, the outer circumference surface of the distal end of the holding part 5 comes into contact with the inner surface of the elastic cylindrical body 11. The distal end of the holding part 5 is sealed by the elastic cylindrical body 11. Whereby, the injection needle 4 is covered by the cap 2. Thus, the cap 2 is mounted to the syringe body 1 without being tilted.

According to the thus described syringe, the guide part 19 formed on the external cylindrical body 12 comes into contact with a part of the syringe body 1 so that the injection needle 4 is guided into the inside the elastic cylindrical body 11 while being prevented from being tilted obliquely. Whereby, it is possible to prevent the cap 2 from being mounted to the syringe body 1 at an oblique angle to the syringe body 1.

A plurality of ridges which project radially inwardly from the inner surface of the guide part 19 may be formed. The plurality of ridges are preferably formed at intervals in the inner circumferential direction of the guide part 19. The plurality of ridges preferably have elongated rib shape extending along the tube axis direction of the guide part 19. With forming the ridges on the inner surface of the guide part 19, it is possible to decrease the contact area between the inner surface of the guide part 19 and the outer surface of the tubular part 6 as compared with the case where the inner surface of the guide part 19 is in surface-to-surface contact with the outer surface of the tubular part 6 of the syringe body 1. Accordingly, it is possible to reduce the friction force acting between the guide part 19 and the tubular part 6, and thereby enable easy attachment of the cap 2 to the syringe body 1.

A plurality of ridges may be formed on the outer surface of the tubular part 6 formed on the syringe body 1 in the same manner as the above. In this case, it is preferable that the plurality of ridges be formed at intervals in the outer circumferential direction of the tubular part 6. The plurality of ridges preferably have an elongated rib shape extending in the tube axis direction of the tubular part 6. With forming the plurality of ridges on the outer surface of the tubular part 6, it is possible to decrease the contacting area between the inner surface of the guide part 19 and the outer surface of the tubular part 6 as compared with the case where the inner surface of the guide part 19 is in surface-to-surface contact with the outer surface of the tubular part 6 of the syringe body 1. Accordingly, it is possible to reduce the friction force acting between the guide part 19 and the tubular part 6, and thereby enable easy attachment of the cap 2 to the syringe body 1. These ridges may be formed on both of the guide part 19 and the tubular part 6, or on any one of the guide part 19 and the tubular part 6.

Figure 2:
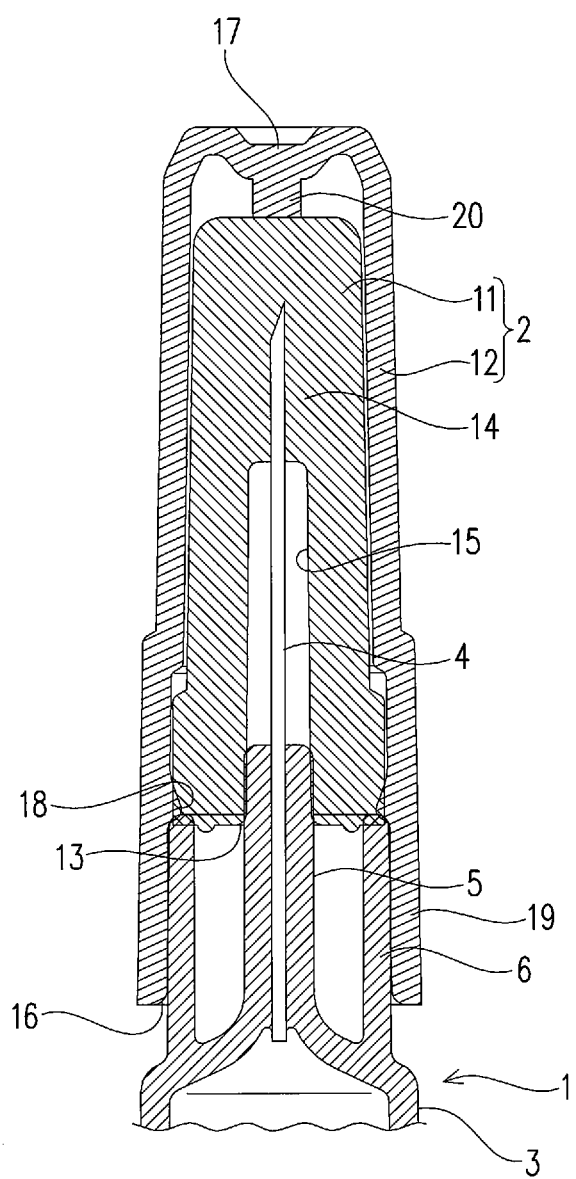
FIG. 2 is a cross sectional view showing a second embodiment of the syringe according to the present invention.

FIG. 2 shows a second embodiment of the syringe according to the present invention. In the present embodiment, the shape of the external cylindrical body 12 of the cap 2 is different from that of the first embodiment of FIG. 1. In the present embodiment, a protrusion 20 is formed on the closing part 17 of the external cylindrical body 12. The protrusion 20 is provided at a certain position of the inner surface of the external cylindrical body 12, that is, inside the external cylindrical body 12 so as to have its axis matching the tube axis of the external cylindrical body 12. The protrusion 20 protrudes toward the inner side in the tube axis direction of the external cylindrical body 12, that is, toward the opening part 16 from the closing part 17 of the external cylindrical body 12. The external cylindrical body 12 holds the elastic cylindrical body 11 with the protrusion 20 and the locking ridge 18 sandwiching the elastic cylindrical body 11.

The distance between the protrusion 20 and the locking ridge 18 is smaller than the length (entire length) of the elastic cylindrical body 11. Thus, the elastic cylindrical body 11 is compressed with the protrusion 20 and the locking ridge 18 along the axial direction when it is sandwiched by the protrusion 20 and the locking ridge 18. At this time, the elastic cylindrical body 11 is elastically deformed so as to expand in the radial direction. Whereby, the elastic cylindrical body 11 comes into tight contact with the inner surface of the external cylindrical body 12. The friction force exerted by this tight contact and the locking ridge 18 enables the elastic cylindrical body 11 to be held inside the external cylindrical body 12 while preventing the elastic cylindrical body 11 from slipping out from the external cylindrical body 12.

The elements, members or parts of the present embodiment, which are the same as those of the first embodiment, are allocated the same reference numbers (the same also applicable to the following embodiments).

Figure 3:
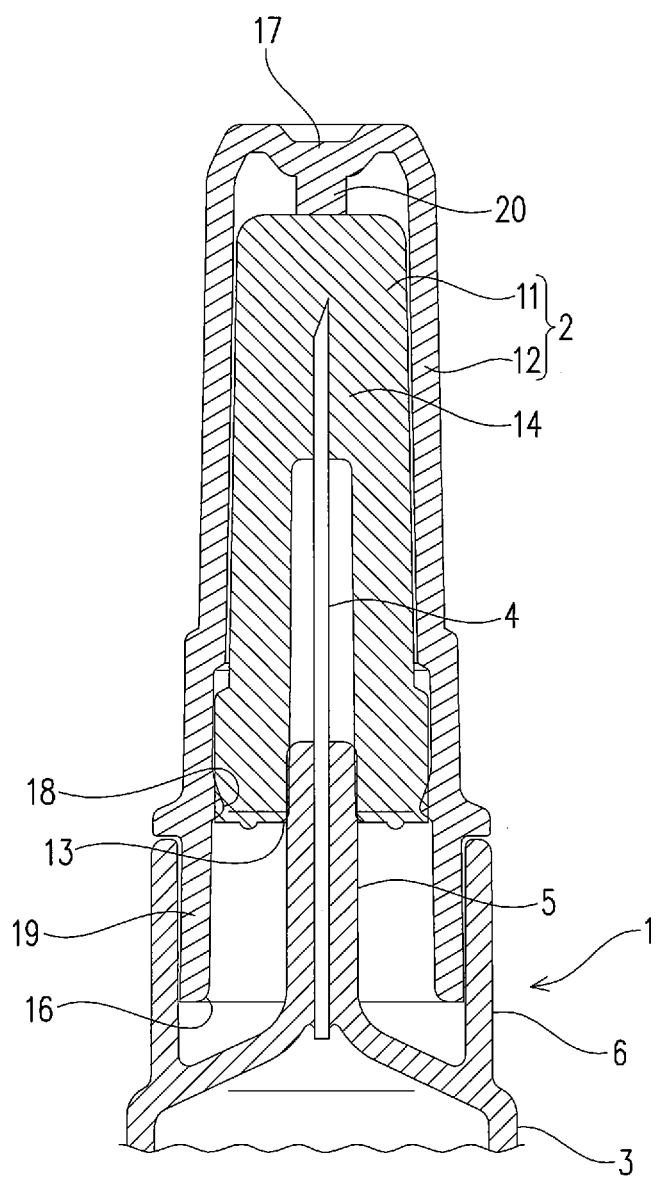
FIG. 3 is a cross sectional view showing a third embodiment of the syringe according to the present invention.

FIG. 3 shows a third embodiment of the syringe according to the present invention. In the present embodiment, the shape of the external cylindrical body 12 of the cap 2 is different from that of the second embodiment. In the present embodiment, the external cylindrical body 12 is configured to be inserted into the inside the tubular part 6 formed on the syringe body 1. Specifically, the outer diameter of the guide part 19 of the external cylindrical body 12 is configured to be substantially equal to the inner diameter of the tubular part 6 of the syringe body 1. Whereby, the outer surface (outer circumferential surface) of the guide part 19 comes into contact with the inner surface of the tubular part 6 formed in the syringe body 1. Thus, the cap 2 enables the injection needle 4 to be guided into the elastic cylindrical body 11 without being tilted.

Figure 4:
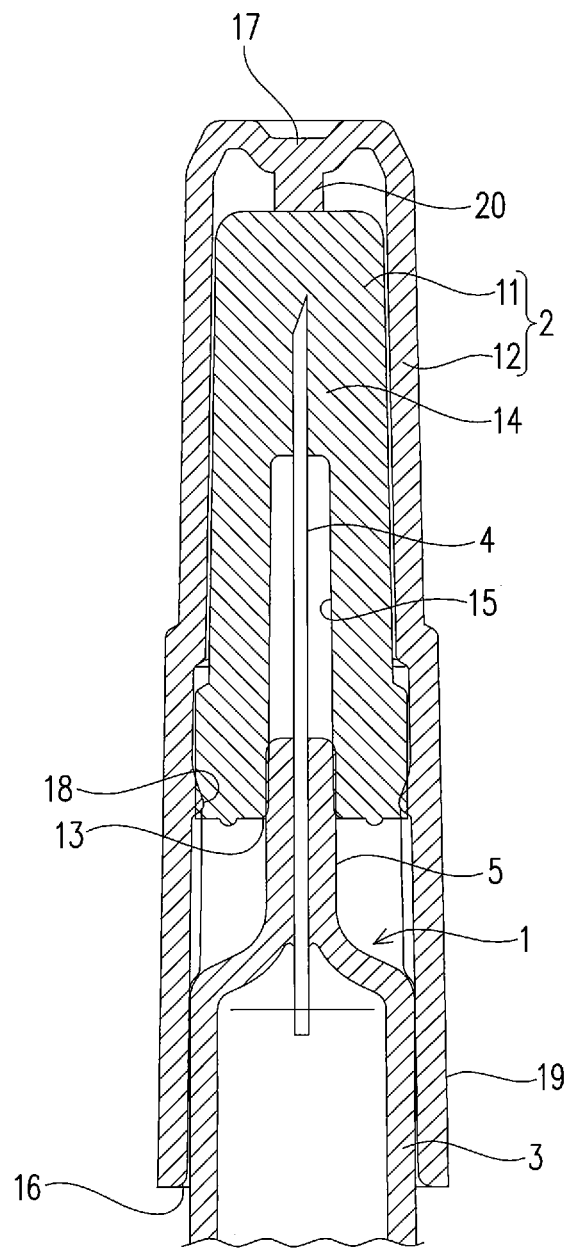
FIG. 4 is a cross sectional view showing a fourth embodiment of the syringe according to the present invention.

FIG. 4 shows a fourth embodiment of the syringe according to the present invention. In the present embodiment, the shape of the syringe body 1 is different from that of the first embodiment. In the first embodiment, the description was made by taking, for example, the case where the tubular part 6 which contacts the guide part 19 of the cap 2 is formed on the syringe body 1, while, in the present embodiment, the tubular part 6 is not formed on the syringe body 1. In the present embodiment, the inner diameter of the guide part 19 is configured to be substantially equal to the outer diameter of the shank 3 of the syringe body 1. The guide part 19 comes into contact with the outer surface of the shank 3 of the syringe body 1 so that the injection needle 4 can be guided in a certain direction without being tilted. Whereby, the cap 2 is mounted to the syringe body 1 without being tilted.

Figure 5:
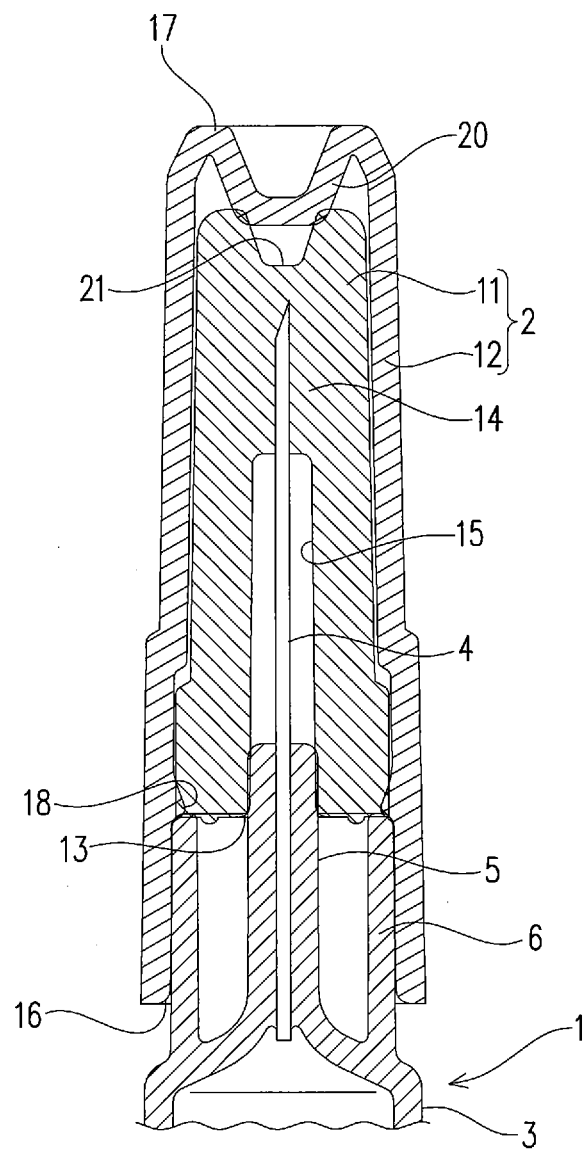
FIG. 5 is a cross sectional view showing a fifth embodiment of the syringe according to the present invention.

FIG. 5 shows a fifth embodiment of the syringe according to the present invention. In the present embodiment, the shapes of the external cylindrical body 12 and the elastic cylindrical body 11 are different from those of the first embodiment. In the present embodiment, the elastic cylindrical body 11 has a recess 21 on a top surface of the distal end. The external cylindrical body 12 has a protrusion 20 for pressing an edge of the recess 21. The distance between the protrusion 20 and the locking ridge 18 formed on the inner surface of the external cylindrical body 12 is configured to be smaller than the length of the elastic cylindrical body 11.

The cap 2 is configured so that, when the elastic cylindrical body 11 is inserted into the inside the external cylindrical body 12, the protrusion 20 of the external cylindrical body 12 presses the edge of the recess 21 of the elastic cylindrical body 11. Whereby, the end portion of the elastic cylindrical body 11 in which the recess 21 is formed is deformed so as to expand in the radial direction and comes into tight contact with the inner surface of the external cylindrical body 12. The friction force exerted by this contact enables the elastic cylindrical body 11 to be securely held within the external cylindrical body 12.

Figure 6:
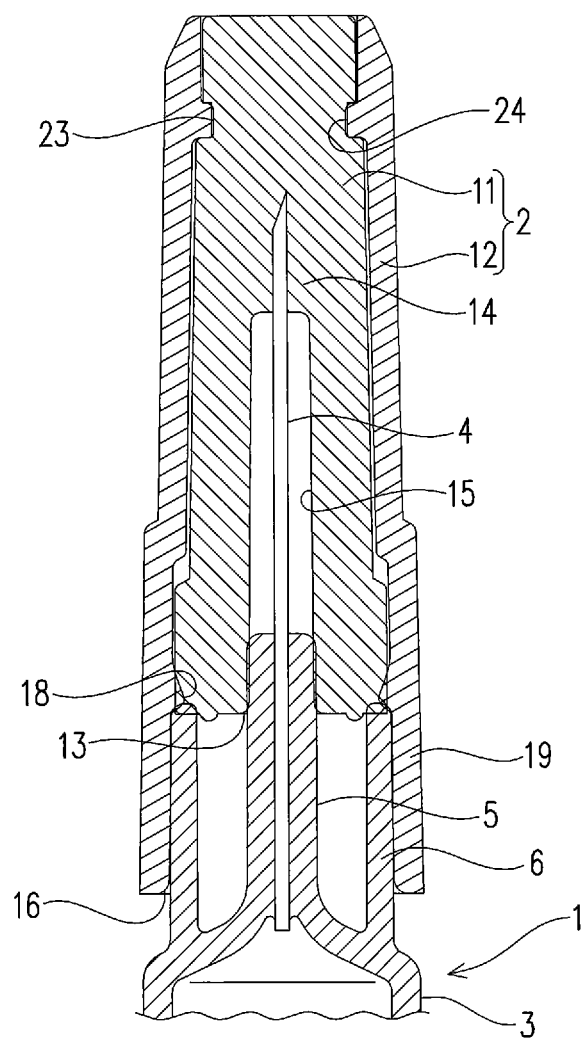
FIG. 6 is a cross sectional view showing a sixth embodiment of the syringe according to the present invention.

FIG. 6 shows a sixth embodiment of the syringe according to the present invention. In the present embodiment, the shapes of the elastic cylindrical body 11 and the external cylindrical body 12 are different from those of the first embodiment. An annular recess (groove) 23 is formed at an intermediate portion of the outer surface of the elastic cylindrical body 11. A ridge 24 is formed on the external cylindrical body 12 so as to be fitted into the recess 23. The ridge 24 has an annular shape formed along the circumferential direction of the inner surface of the external cylindrical body 12. The elastic cylindrical body 11 is held within the external cylindrical body 12 by the fitting engagement of the ridge 24 into the recess 23, and the locking ridge 18.

Figure 7:
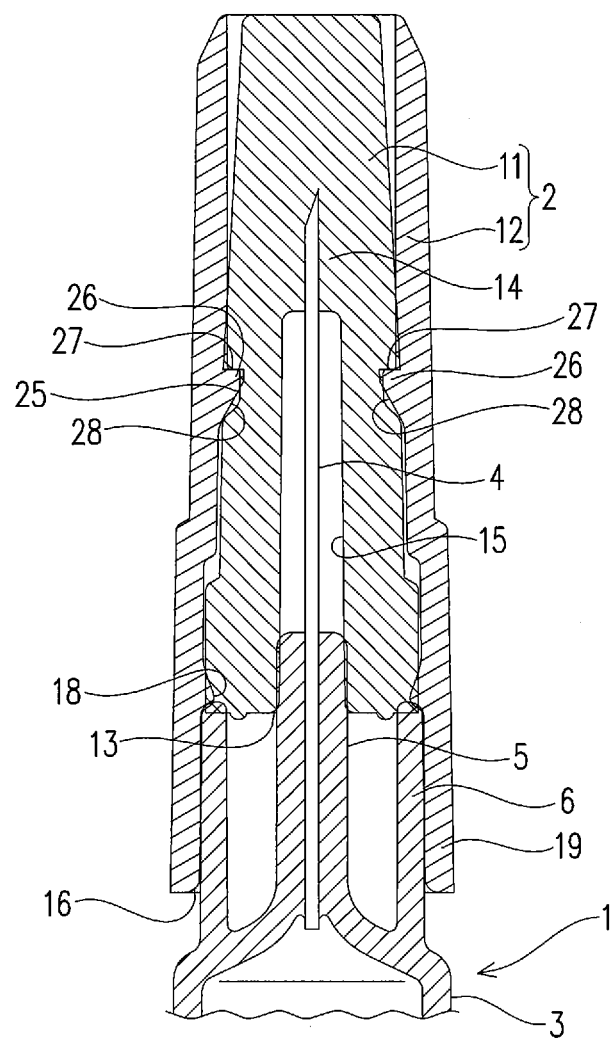
FIG. 7 is a cross sectional view showing a seventh embodiment of the syringe according to the present invention.
Figure 8:
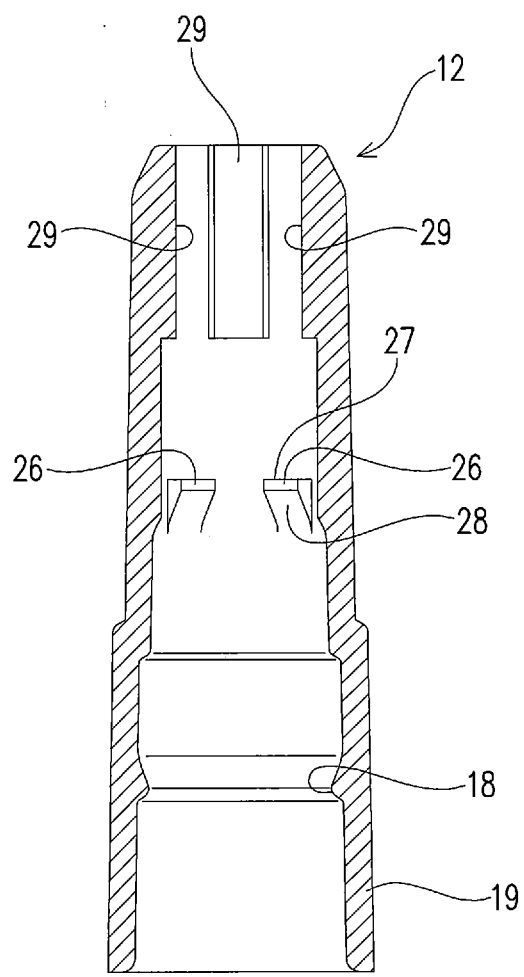
FIG. 8 is a cross sectional view showing a modified example of the seventh embodiment of the syringe according to the present invention.

FIG. 7 and FIG. 8 show a seventh embodiment of the syringe according to the present invention. In the present embodiment, the shape of the cap 2 is different from that of the first embodiment.

In the present embodiment, the elastic cylindrical body 11 has a recess 25 at an intermediate position of its outer surface. The elastic cylindrical body 11 is configured to have a tapered portion on the distal end side of the recess 25.

The external cylindrical body 12 does not have the closing part 17 described in the first embodiment. The external cylindrical body 12 has a ridge 26 that fits into the recess 25 of the elastic cylindrical body 11 to come into locking engagement with the elastic cylindrical body 11. The ridge 26 has a locking surface 27 for coming into locking engagement with the recess 25 of the elastic cylindrical body 1, and an inclined surface 28 provided adjacent to the locking surface 27.

In the cap 2 of the present embodiment, a part of the elastic cylindrical body 11 has a tapered shape, and the inclined surface 28 is formed at the ridge 26 of the external cylindrical body 12, so that the friction force acting between the elastic cylindrical body 11 and the external cylindrical body 12 can be reduced when the elastic cylindrical body 11 is inserted into the external cylindrical body 12. Whereby, the elastic cylindrical body 11 can be easily arranged at a certain position within the external cylindrical body 12.

FIG. 8 shows a modified example of the external cylindrical body 12 in the seventh embodiment. In this modified example, a plurality of ridges 29 are further formed on the inner surface of the distal end portion of the external cylindrical body 12. These ridges 29 have a rib shape elongated in the tube axis direction of the external cylindrical body 12. With the plurality of ridges 29 formed in this manner, it is possible to increase the contact area between the elastic cylindrical body 11 and the external cylindrical body 12. Whereby, the elastic cylindrical body 11 can be securely held within the external cylindrical body 12.

Figure 9:
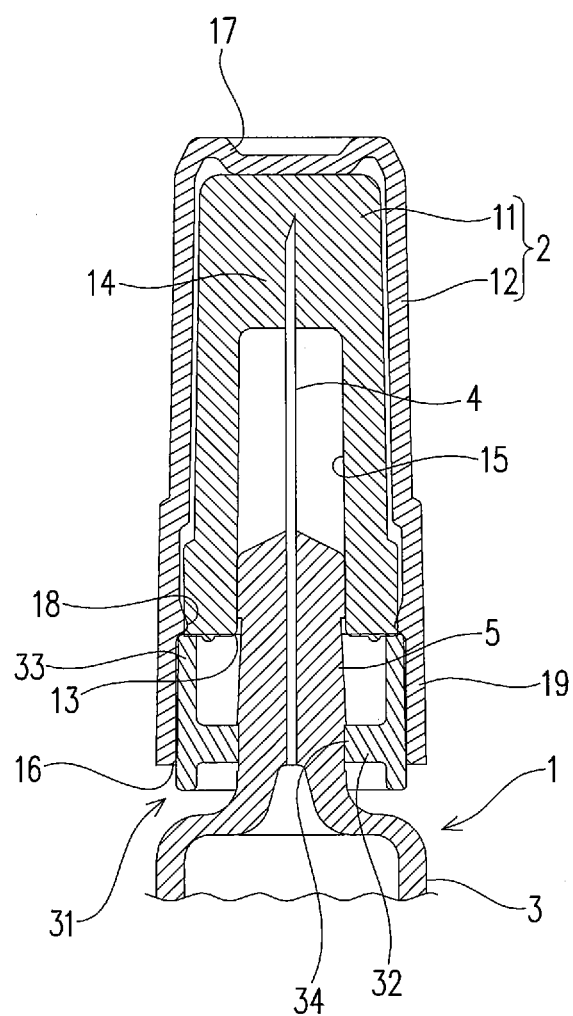
FIG. 9 is a cross sectional view showing an eighth embodiment of the syringe according to the present invention.

FIG. 9 shows an eighth embodiment of the syringe according to the present invention. In the present embodiment, the shape of the syringe body 1 is different from that of the first embodiment. In the present embodiment, the syringe body 1 includes an adapter 31 for mounting the cap 2. The adapter 31 includes a mounting part 32 to be mounted to the syringe body 1, and a tubular part 33 that contacts the holding part 5 of the cap 2. The mounting part 32 has a through-hole 34 through which the holding part 5 of the syringe body 1 passes. The adapter 31 is attached to the syringe body 1 by the holding part 5 of the syringe body 1 passing through the through-hole 34 of the mounting part 32.

The tubular part 33 has a cylindrical shape. The outer diameter of the tubular part 33 is configured to be substantially equal to the inner diameter of the guide part 19 formed on the external cylindrical body 12 of the cap 2. In the present embodiment, the outer surface of the tubular part 33 of the adapter 31 comes into contact with the inner surface of the guide part 19 formed on the external cylindrical body 12 of the cap 2, and thus the cap 2 is guided therealong, so that the cap 2 is appropriately mounted to the syringe body 1 without being tilted.

Figure 10:
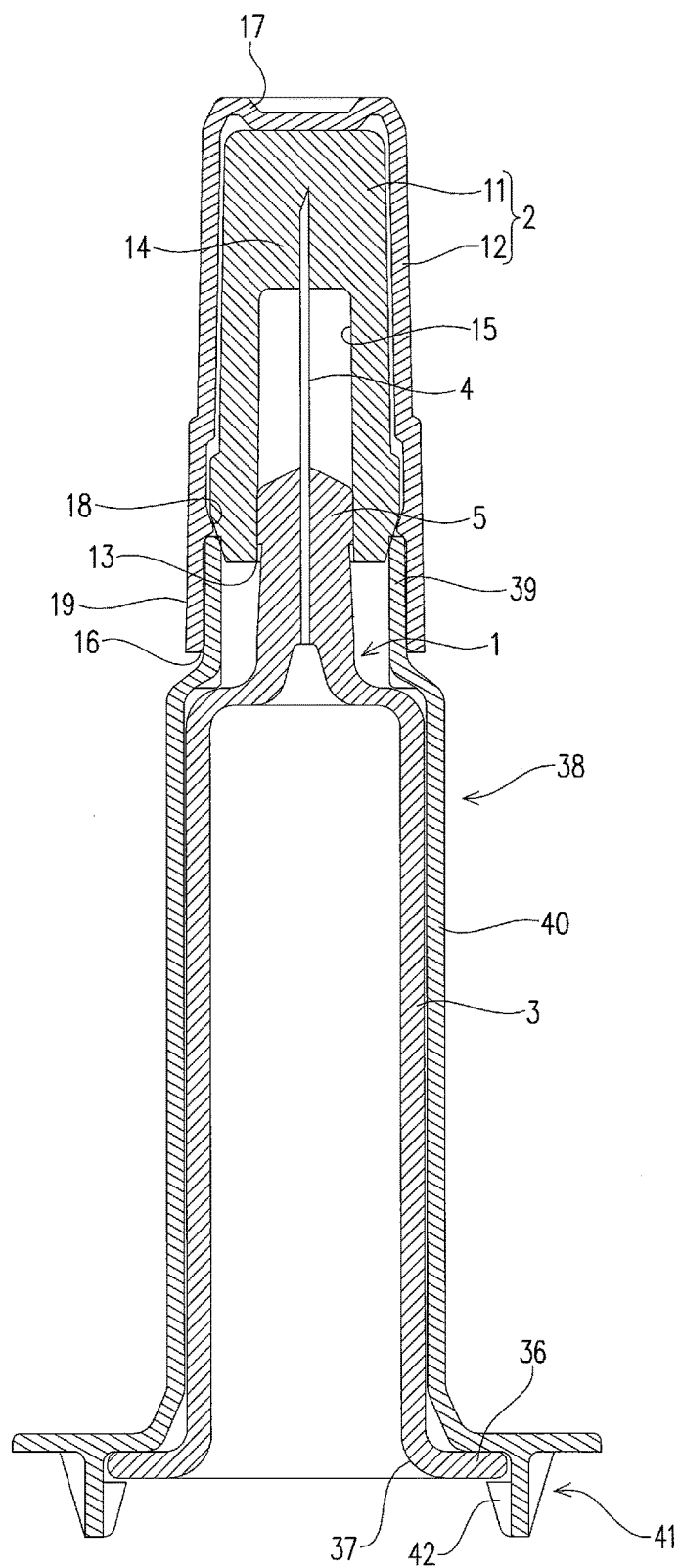
FIG. 10 is a cross sectional view showing a ninth embodiment of the syringe according to the present invention.

FIG. 10 shows a ninth embodiment of the syringe according to the present invention. In the present embodiment, the shape of the syringe body 1 is different from that of the first embodiment. In the present embodiment, the syringe body 1 has one end provided with the holding part 5 for holding the injection needle 4, and another end provided with a flange 36 and an opening part 37. The syringe body 1 further includes a cover 38 for covering the syringe body 1.

The cover 38 is made of a transparent resin and formed into a tubular shape. The cover 38 includes a first tubular part 39, a second tubular part 40 having a diameter larger than the first tubular part 39, and a mounting part 41 for mounting the cover 38 to the syringe body 1.

The first tubular part 39 has a cylindrical shape. The inner diameter of the first tubular part 39 is configured to be larger than the outer diameter of the holding part 5. When the cover 38 is attached to the syringe body 1, the first tubular part 39 covers a part of the holding part 5. The length of the first tubular part 39 in the tube axis direction is configured to be smaller than the length of the holding part 5. Accordingly, when the cover 38 is attached to the syringe body 1, the distal end of the holding part 5 projects further outward compared with the distal end of the first tubular part 39.

The second tubular part 40 is configured to cover the shank 3 of the syringe body 1. The second tubular part 40 has a cylindrical shape.

The mounting part 41 is provided at one end of the second tubular part 40. The mounting part 41 is configured to cover the flange 36 of the syringe body 1. The mounting part 41 includes a locking part 42 for coming into locking engagement with the flange 36 of the syringe body 1.

In the present embodiment, the outer surface of the first tubular part 39 formed on the cover 38 comes into contact with the inner surface of the guide part 19 formed on the cylindrical body 12 of the cap 2 so that the injection needle 4 can be guided to a certain direction without being tilted. Whereby, the cap 2 is mounted to the syringe body 1 without being tilted.

Figure 11:
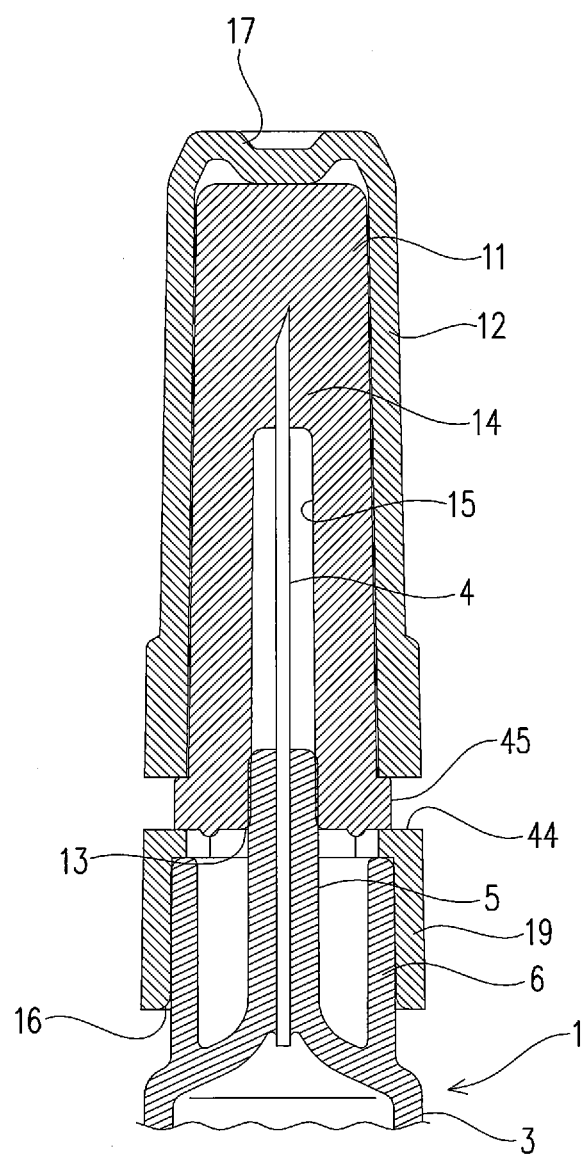
FIG. 11 is a cross sectional view showing a tenth embodiment of the syringe according to the present invention.

FIG. 11 shows a tenth embodiment of the syringe according to the present invention. In the present embodiment, the shape of the cap 2 is different from that of the first embodiment. In the present embodiment, a through-hole 44 passing through the inside and outside of the external cylindrical body 12 is formed at an intermediate portion of the external cylindrical body 12. A ridge 45 is formed on the elastic cylindrical body 11 so as to project radially outwardly to pass through the through-hole 44. In the present embodiment, the locking ridge 18 as described in the first embodiment is not formed on the inner surface of the external cylindrical body 12.

In the present embodiment, the ridge 45 of the elastic cylindrical body 11 passes through the through-hole 44 of the external cylindrical body 12 so that the elastic cylindrical body 11 is held by the external cylindrical body 12 so as not to slip out from the external cylindrical body 12.

The syringe of the present embodiment is not necessarily limited to the configurations of the above embodiments. Also, the syringe of the present invention is not necessarily limited to the aforesaid operational effect. The syringe of the present invention can be subjected to various modifications within the gist of the present invention.

REFERENCE SIGNS LIST

1 Syringe Body
2 Cap
3 Shank
4 Injection Needle
5 Holding Part
6 Tubular Part
11 Elastic Cylindrical Body
12 External Cylindrical Body
13 Opening Part
14 Closing Part
15 Insertion Recess
16 Opening Part
17 Closing Part
18 Locking Ridge
19 Guide Part
20 Protrusion
21 Recess
23 Recess
25 Recess
26 Ridge
27 Locking Surface
28 Inclined Surface
29 Ridge
31 Adapter
32 Mounting Part
33 Tubular Part
34 Through-hole
36 Flange
37 Opening Part
38 Cover
39 First Tubular Part
40 Second Tubular Part
41 Mounting Part
42 Locking Part
44 Through-hole
45 Ridge

The invention claimed is:

1. A syringe comprising a syringe body that includes a holding part for holding an injection needle, and a cap for covering the injection needle,
  the cap comprising an elastic cylindrical body that is configured to allow the injection needle to pierce thereinto, receive the piercing injection needle therein and seal the holding part, and an external cylindrical body for covering the circumference of the elastic cylindrical body and holding the elastic cylindrical body in such a manner as to prevent movement of the elastic cylindrical body, and
  the external cylindrical body comprising an opening part having a dimension configured to be larger than the holding part of the syringe body, and a guide part that comes into contact with a part of the syringe body before the injection needle pierces into the elastic cylindrical body, and allows the injection needle to be received inside the elastic cylindrical body while guiding the injection needle toward a certain direction by the contact of the guide part with the part of the syringe body, wherein
  the part of the syringe body that is configured to contact the guide part is arranged around the holding part and radially outward of the holding part, and
  the guide part and the part of the syringe body that is configured to contact the guide part are both formed in a cylindrical shape.

2. The syringe according to claim 1, wherein the guide part includes a ridge for contacting a part of the syringe body.

3. The syringe according to claim 1, wherein the syringe body includes a ridge for contacting the guide part.

4. The syringe according to claim 1, wherein the external cylindrical body has one end provided with the opening part therein, and another end provided with a closing part,
  wherein the external cylindrical body includes a protrusion that protrudes inwardly from the closing part in the tube axis direction of the external cylindrical body, and a locking ridge that comes into locking engagement with the elastic cylindrical body to lock the elastic cylindrical body at a certain position of an inner surface of the external cylindrical body, the certain position being distant from the protrusion,
  wherein the external cylindrical body holds the elastic cylindrical body with the protrusion and the locking ridge sandwiching the elastic cylindrical body, and
  wherein a distance between the protrusion and the locking ridge is smaller than a length of the elastic cylindrical body.

5. The syringe according to claim 1, wherein the syringe body is made of cycloolefin polymer.

6. The syringe according to claim 1, wherein the holding part further projects toward a distal end side of the injection needle than the part of the syringe body.

7. The syringe according to claim 1, wherein the external cylindrical body is mounted to the syringe body by sliding the guide part and the part of the syringe body, both of which have a cylindrical shape, along the axial direction of the injection needle.

8. The syringe according to claim 1, wherein a distal end of the part of the syringe body and an end of the elastic cylindrical body are configured to abut each other in the axial direction of the injection needle when the cap is mounted to the syringe body.

9. A syringe comprising a syringe body that includes an injection needle, and a cap for covering the injection needle,
  the cap comprising an elastic cylindrical body that is configured to allow the injection needle to pierce thereinto, and an external cylindrical body for covering the circumference of the elastic cylindrical body and holding the elastic cylindrical body in such a manner as to prevent movement of the elastic cylindrical body,
  the external cylindrical body comprising a guide part that comes into contact with a part of the syringe body to guide the injection needle toward a certain direction, and the syringe body comprising a holding part for holding the injection needle, and a tubular part as the part of the syringe body with which the guide part comes into contact, wherein the tubular part is coaxial with the holding part to cover the holding part, and arranged radially outward thereof, and the elastic cylindrical body is configured to seal the holding part at a position closer to a distal end side of the injection needle than the tubular part when the cap is mounted to the syringe body.

10. The syringe according to claim 9, wherein a distal end of the tubular part and an end of the elastic cylindrical body are configured to abut each other when the cap is mounted to the syringe body.

\* \* \* \* \*